United States Patent
Hoshino et al.

(10) Patent No.: US 6,460,401 B1
(45) Date of Patent: Oct. 8, 2002

(54) METHOD AND APPARATUS FOR TRACE ANALYSIS OF ORGANIC COMPOUND

(75) Inventors: Kunihiro Hoshino; Yoshihiko Takano; Takeshi Miyabayashi, all of Tokyo (JP)

(73) Assignee: GL Science Inc. (JP)

( * ) Notice: Subject to any disclaimer, the term of this patent is extended or adjusted under 35 U.S.C. 154(b) by 0 days.

(21) Appl. No.: 09/461,998

(22) Filed: Dec. 15, 1999

(30) Foreign Application Priority Data

Dec. 22, 1998 (JP) .......................................... 10-364806

(51) Int. Cl.[7] .......................... G01N 30/08; G01N 1/00; G01N 1/28
(52) U.S. Cl. ..................... 73/23.35; 73/23.41; 73/23.42; 95/87; 95/115; 96/101; 422/89; 436/161
(58) Field of Search .............................. 73/23.35, 23.37, 73/23.41, 23.42; 422/68.1, 69, 78, 80, 82, 89; 436/161; 95/87, 115, 141, 143; 96/101, 143, 144, 146

(56) References Cited

U.S. PATENT DOCUMENTS

| | | | | |
|---|---|---|---|---|
| 5,442,949 A | * | 8/1995 | Kinoshita et al. | 73/23.35 |
| 5,522,918 A | * | 6/1996 | Shiramizu | 95/87 |
| 5,569,837 A | * | 10/1996 | Hinaga | 73/19.01 |
| 6,125,689 A | * | 10/2000 | Graves et al. | 73/23.37 |

FOREIGN PATENT DOCUMENTS

| | | | | |
|---|---|---|---|---|
| JP | 4-359149 | * | 12/1992 | 436/161 |
| JP | 5-157742 | * | 6/1993 | 73/23.35 |
| JP | 5-232095 | * | 9/1993 | 73/864.73 |
| JP | 5-256842 | * | 10/1993 | 73/61.52 |

* cited by examiner

Primary Examiner—Daniel S. Larkin
(74) Attorney, Agent, or Firm—Scott M. Oldham; Hahn Loeser + Parks LLP

(57) ABSTRACT

The invention relates to a method of trace analysis of organic compounds which calls for the steps of setting a test piece in a flow cell, and thereafter removing organic compounds from the test piece by heating it at high temperature in an oven. The compounds are concentrated in a trap tube and then removed from the trap tube and carried into a concentrating/inlet unit, such as a thermal desorption cold trap injector. In this unit, cryofocusing of the compounds is performed, and then the organic compounds are introduced into a gas chromatograph to be analyzed therein, wherein a part of the purified inert gas is caused, except during the process of trapping the organic compounds, to flow into the flow cell from the direction opposite the direction from which the gas flows along the trapping line. The invention also provides an apparatus to be used for the method, including an analyzer having a flow cell, a trap tube connected to the flow cell, a detector connected to the trap tube, and a flow rate controller connected to the flow cell. This can be brought into communication with the trap tube and is so formed as to permit a test piece, such as a wafer, to be removably set therein and also permit a carrier gas to flow therethrough. A channel for purified inert gas is provided between the flow rate controller and the flow cell and also between the flow rate controller and a valve that communicates with the flow cell.

4 Claims, 3 Drawing Sheets

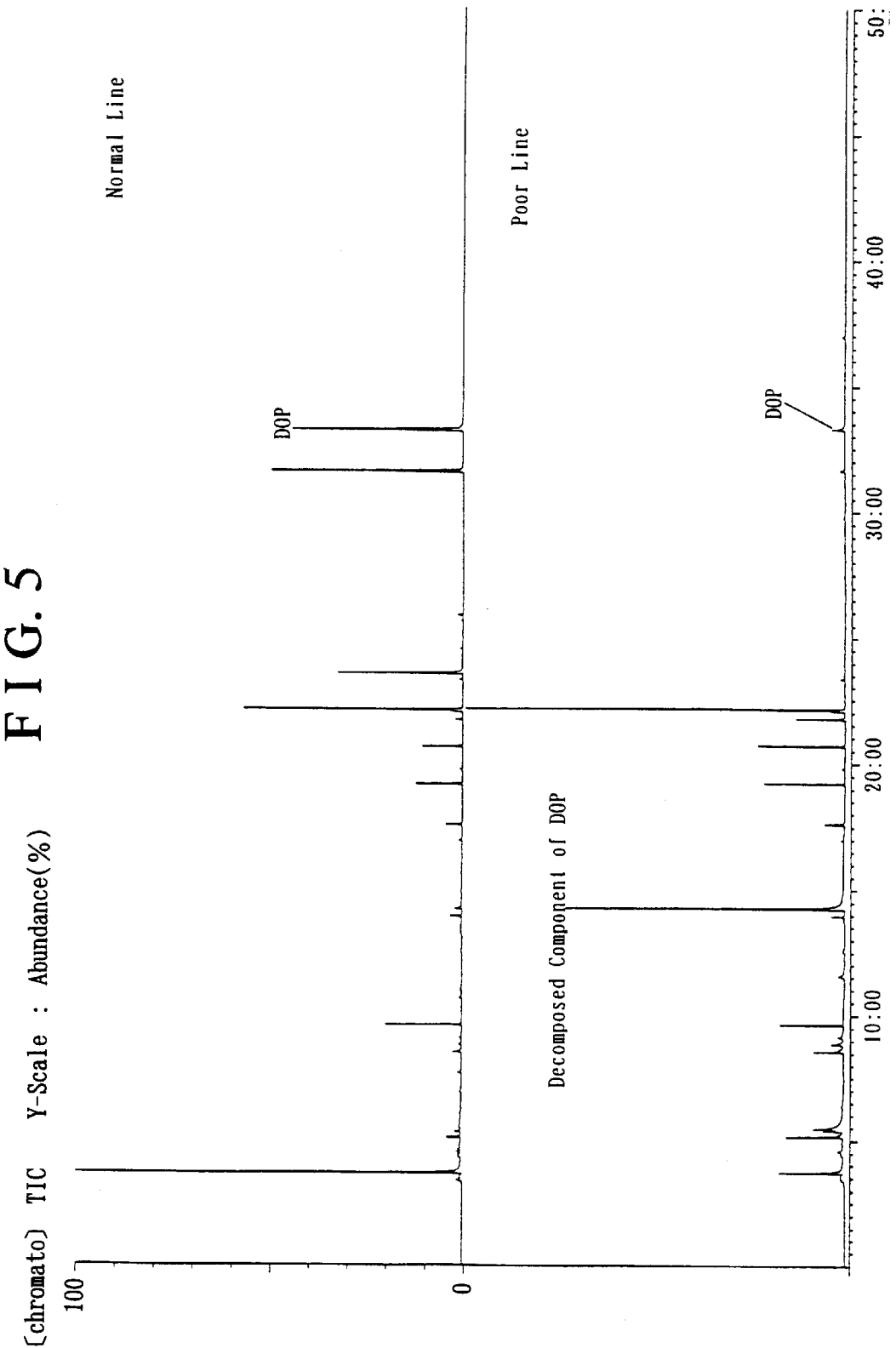

METHOD AND APPARATUS FOR TRACE ANALYSIS OF ORGANIC COMPOUND

FIELD OF THE INVENTION

The present invention relates to a method and an apparatus for trace analysis of organic compounds. The invention is particularly effective for analysis of organic compounds adhering to a silicone wafer, an electronic substrate,or the like.

BACKGROUND OF THE INVENTION

It is a common practice to wash out organic compounds, such as dirt and microorganisms, that are attached to the surface of a silicone wafer or its plastic package with a chlorofluorocarbon, such as FREON or a substitute therefor. Such a washing process, however, presents the problem of a residual solvent. Even if it is washed with pure water, a very small quantity of the organic compounds are prone to remaining. Furthermore, in case of an electronic substrate, the problem of evaporation of a volatile solvent often arises during operation of the apparatus in which the electronic substrate is set, because the heat generated by the operation of the apparatus causes the evaporation of the solvent.

Conventionally, such an organic compound cannot be measured, because its density is so low that it would need to be represented in terms of ppb or ppt. Therefore, such a measurement is not conducted in reality. Even if it were to be measured, it would be extremely difficult and would have to be done manually.

Adhesion of organic compounds to the surface of a silicone wafer or the like is a major cause of defective products among semiconductor products, such as IC's and LSI's. As these semiconductor products are mass-produced automatically, defective products sometimes result in a tremendous loss.

In order to solve the above problems by providing a means of analyzing such a small quantity of organic compound, the applicant of the present invention had previously developed a method and an apparatus for trace analysis of organic compounds adhering to a silicone wafer or a similar object, wherein a completely automatic analysis is performed once a test piece is set in the apparatus. The applicant filed patent applications for said method and apparatus under Patent Applications Ser. Nos. 1992–88105 and 1993–97243.

Although the aforementioned invention is very effective as a means of trace analysis of organic compounds, it presents a problem in that the gas in the apparatus flows only in one direction, from the flow cell toward the valves. Due to this feature, there is the possibility of such undesirable elements as air, the blank gas, or interfering particles entering the line when the flow cell is open or in other occasions. It is prone to causing a serious problem particularly when the apparatus is used at high temperature, such as a case where the apparatus is used for analysis of a substance that volatizes at high temperature, because the air entering the system causes oxidation of communication passages or other parts of the apparatus and sometimes necessitates replacement of the entire passage. The above invention presents another problem in that it is not capable of completely protecting the communication passages or other parts from contamination by various substances during hot washing of the flow cell, which is typically performed after using a dirty test piece.

SUMMARY OF THE INVENTION

Accordingly, the present invention relates to a method of trace analysis of organic compounds which calls for setting a test piece in a flow cell, removing organic compounds from the test piece by heating it at high temperature in an oven, concentrating the compounds in a trap tube and removing the compounds from the trap tube, carrying the organic compounds into a concentrating/inlet unit, such as a thermal desorption cold trap injector, to perform cryofocusing of the compounds, and then introducing the organic compounds into a gas chromatograph to be analyzed therein, wherein a part of the purified inert gas is caused, except during the process of trapping the organic compounds, to flow into the flow cell from the direction opposite the direction from which the gas flows along the trapping line. As an apparatus to be used for said method, the invention also provides an analyzer that comprises a flow cell, a trap tube connected to the flow cell, a detector connected to the trap tube, and a flow rate controller connected to the flow cell, which can easily be brought into communication with said trap tube and is so formed as to permit a test piece, such as a wafer, to be removably set therein and also permit a carrier gas to flow therethrough, wherein a channel for purified inert gas is provided between the flow rate controller and the flow cell and also between the flow rate controller and a valve that communicates with the flow cell. According to another feature of the invention, the aforementioned channel for the inert gas is connected to a plurality of flow cells, and/or the channel for the inert gas is connected to a plurality of trap tubes.

BRIEF DESCRIPTION OF THE DRAWINGS

FIG. 5 is a chromatogram representing the performance of an embodiment of the invention.

DETAILED DESCRIPTION OF THE INVENTION

Figure 1:
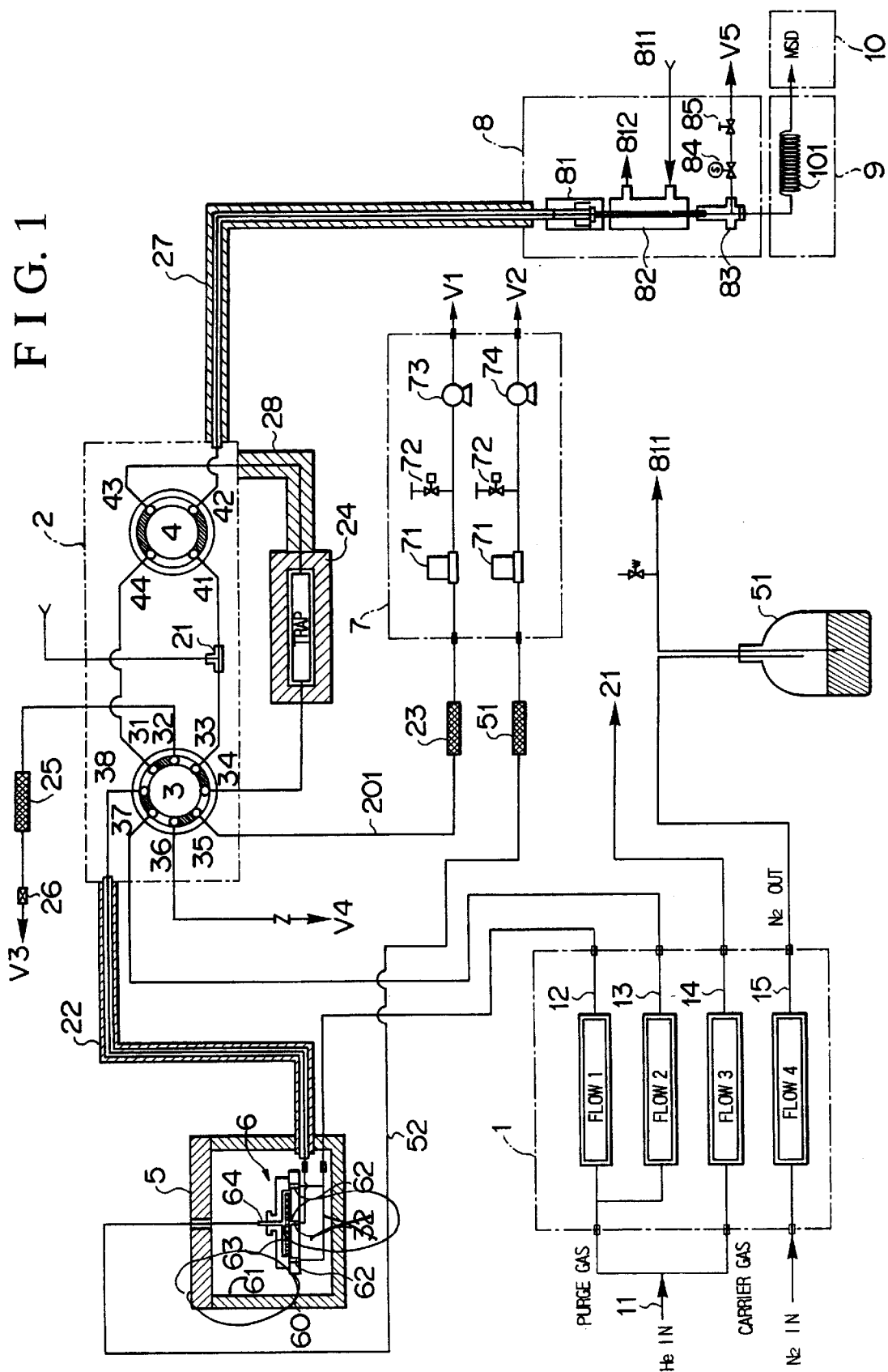
FIG. 1 is a schematic illustration of an embodiment of the present invention.

The present invention is explained in detail hereunder, referring to FIG. 1 which represents a schematic illustration of an embodiment of the invention. Numeral 1 denotes a flow rate controller adapted to control the flow of various components, such as a cell purge gas channel 12, a carrier gas channel 14, a nitrogen gas feeding channel 15, and instrument control channels (not shown) that may be provided whenever necessary. If it is necessary, each channel may advisably be provided with a stop valve, a pressure governor, a flow rate indicator, and/or any other necessary components according to methods known to those skilled in the art. In case of this embodiment, the carrier gas channel 14 for passing the carrier gas, such as helium, includes a stop valve and/or any other necessary components mentioned above. The carrier gas channel 14 extends from an inlet port 11 and is connected to a T-joint 21, which is disposed about halfway between selector valves 3,4 that are installed in a valve oven 2. The cell purge gas channel 12 for passing the cell purge gas, such as helium, includes a stop valve and/or any other necessary components mentioned above. The cell purge gas channel 12 extends from the inlet port 11 and is connected to supply ports 62,62, . . . of the cell body 60 of a flow cell 6, which is installed in an electric oven 5. The cell purge gas channel 12 is branched at some point along the line. The branched portion is formed into the cell purge gas channel 13 that communicates with a selector port 37 of the selector valve 3 in the valve oven 2. As mentioned above, the flow rate controller 1 is also provided with the container pressurizing nitrogen gas feeding channel 15 for feeding liquid nitrogen, which is used as a coolant, by siphonage to a concentrating/inlet unit, which is a thermal desorption cold trap injector (hereinafter called TCT) in case of the present embodiment. If it is necessary, the flow rate controller 1 may also include an air channel (not shown) for controlling the various gauges or other instruments.

The valve oven 2 has the aforementioned selector valves 3,4. The selector valve 3 is provided with selector ports 31, 32, 33, 34, 35, 36, 37, 38, while the selector valve 4 is provided with selector ports 41, 42, 43, 44, and they are connected as follows: the selector port 38 of the selector valve 3 is connected to the flow cell 6 in the electric oven 5 via a communicating tube 22, which can easily be controlled by a heating device, such as a heater; the selector port 36 is connected to a vent V4; the selector port 37 is connected to the cell purge gas channel 13 as described above; the selector port 35 is connected to a discharge line 201, which extends via a charcoal filter 23 to a flow indicator 71 installed in a flow rate controller 7, and then via a pump 73 to a vent V1; the selector port 34 is connected via a trap tube 24 to the selector port 43 of the selector valve 4; the selector port 42 of the selector valve 4 communicates with the TCT 8; the selector port 33 communicates with the selector port 41 of the selector valve 4; the selector port 31 is connected to the selector port 44 of the selector valve 4; and the selector port 32 is connected to a vent V3 via a charcoal filter 25 and a constant flow valve 26.

The flow cell 6 is installed in a heating furnace, which is the electric oven 5 in the case of the present embodiment. The flow cell 6 consists of a cell body 60 and a cover 61, which are formed of quartz, stainless steel or any other heat resisting material so that organic compounds adhering to a test piece 63 contained in the flow cell 6 can be removed from the test piece 63 by heating the test piece 63. The flow cell 6 is also provided with a discharge line 52, which extends via a charcoal filter 51 to another flow indicator 71 in the flow rate controller 7, and then via a pump 74 to a vent V2.

The TCT 8 includes a communicating tube 81 that can be warmed, an inlet port 811 for introducing liquid nitrogen coolant fed from the nitrogen gas feeding channel 15 by means of the pressure of the nitrogen gas fed through its pressure governor to a liquid nitrogen reservoir 51; a cold trap 82 having a discharge port 812 for discharging the gasified nitrogen; and a T-joint 83. The communicating tube 81, the cold trap 82 and the T-joint 83 are connected in series. A gas chromatograph 9, to which a capillary column 101 is connected, and a detector 10, which may be a mass spectrometer, are connected in series with the TCT 8. The T-joint 83 communicates with a vent V5 via a solenoid valve 84 and a needle valve 85. It is desirable that temperatures of a path 27 from the selector valve 4 of the valve oven 2 to the TCT 8, a path 28 to the trap tube 24, and the trap tube 24 itself can be controlled separately and independently by using respective heaters or any other appropriate means.

Next, the function of the present invention having the configuration as above is explained hereunder. First, a test piece 63, which may be a wafer or the like, is placed in the flow cell 6, and the flow cell 6 containing the test piece 63 is set in the electric oven 5. The flow rate controller 1 is adjusted so as to flow the cell purge gas, which is pure, inert gas such as helium, through the cell purge gas channel 12, thereby purging the inside of the flow cell 6. The cell gas is also caused to flow from the cell purge gas channel 13 in the sequence of the selector port 37 of the selector valve 3, the selector port 38 of the selector valve 3, and the communicating tube 22 into the flow cell 6. In other words, the gas flowing in the cell purge gas channel 13 is caused to flow in the direction opposite the direction in which the gas flows during the sample trapping process. A part of the cell purge gas having flown from these directions is allowed to seep out of the flow cell 6 and then out of the electric oven 5 so that it is diffused into the atmosphere, while the remaining gas fills the flow cell and is then moved through the discharge line 52 by means of the pump 74 of the flow rate controller 7 until it is discharged from the vent V2. Depending on the kind of the test piece or the purpose of the analysis, it is sometimes unnecessary to operate the pump 74. In such a case, the inside of the flow cell can be purged merely by seepage of the gas from the flow cell.

The carrier gas is caused to flow from the carrier gas channel 14 and branched at the T-joint 21 disposed at the middle of the valve oven 2. One of the two streams of the carrier gas flows in the sequence of the selector port 41 of the selector valve 4, the selector port 42 of the same selector valve and the communicating tube 27 to the TCT 8, from which the gas further flows in the sequence of the gas chromatograph 9, to which the capillary column 101 is connected, and the detector 10, from which the gas is discharged out of the system. The other portion of the carrier gas flows in the sequence of the selector port 33 of the selector valve 3, the selector port 34 of the same selector valve, the trap tube 24, the communicating tube 28, the selector ports 43, 44 of the selector valve 4, the selector ports 31, 32 of the selector valve 3, the charcoal filter 25 and the constant flow valve 26 and is then discharged from the vent V3.

Next, the electric oven 5 is heated in order to remove the organic compounds from the surface of the test piece 63. At that time, the pump 73 of the flow rate controller 7 is operated to change over the selector valve 3 so that the organic compounds are moved together with the cell purge gas through the selector port 38 of the selector valve 3, the selector port 31 of the selector valve 3, and then through the selector ports 44,43 of the selector valve 4 into the trap tube 24, where the organic compounds are collected. If the test piece is, for example, a silicone wafer, the pump 74 may be operated to carry the organic compounds that have been removed from the upper surface of the silicone wafer from a through hole 64, which is formed in the aforementioned cover 61, so that the organic compounds are discharged through the discharge line 52 to the outside of the system, while the organic compounds removed from the lower surface of the silicone wafer are collected through the line described above. Thus, measurement of the concentration of contamination can be conducted for either desired side or both sides of the silicone wafer. At that time, it is possible to communicate a discharge line with either or each one of the two components of the cell, i.e. the cell body 60 and the cover 61, so as to collect the organic compounds from the top and/or the bottom. By means of the pump 73, the remaining compounds are sucked from the selector port 34 and the selector port 35 of the selector valve 3, moved further through the discharge line 201 and then discharged from the vent V1. Thus, what may be called the trapping line in this specification is formed.

Then, the selector valves 3,4 are changed over to permit the carrier gas to flow from the carrier gas channel 14 via the T-joint 21 and the selector ports 33,34 of the selector valve 3 into the trap tube 24 so that the organic compounds that have been collected in the trap tube 24 are moved through the selector ports 43,42 of the selector valve 4 into the TCT 8, where the compounds are moved through the communicating tube 81 into the cold trap 82, in which the compounds are cooled to condense. Thereafter, the cold trap 82 is rapidly heated. The organic compounds are injected into the capillary column 101 in the gas chro-matograph 9, and then carried to the detector 10, which is connected to the capillary column 101. Necessary analysis is conducted in the detector 10. When the injection of the organic compounds is completed, the selector valve 4 is changed over so that the entire flow route is returned to the initial state, i.e. the route for cell purge. Thus, a series of analysis steps are completed.

As described above, except during the process of trapping organic compounds, the inert gas in the cell purge gas channel 13 flows to the selector valve 3, from which it further flows through the selector port 37, 38 of the selector valve 3 and the communicating tube 22 into the flow cell 6, while a part of the inert gas functions as the cell purge gas as it continuously overflows from the gap between the cover 61 and the cell body 60 of the flow cell 6. Therefore, there is no room in the flow cell 6 for the air or any other substances to flow from the outside into the flow cell 6. Even when thermal washing has to be performed after an analysis of a sample that contains a lot of impurities, the cell purge gas fed from the communicating tube 22 ensures the impurities to be discharged, thereby preventing them from entering the flow cell 6. As the quantity of the cell purge gas fed from the communicating tube 22 is minimal, there is no possibility of the cell purge gas exerting any influence on the conditions of use of the communicating tube 22, which is maintained in the temperature range of approximately 200 to 350° C. depending on the object to be analyzed.

Figure 2:
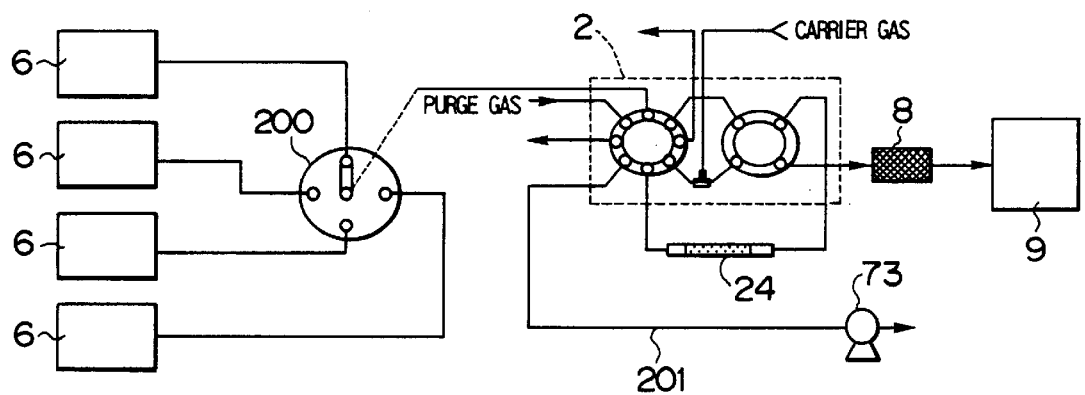
FIG. 2 is an enlarged schematic illustration of the principal part of another embodiment of the present invention.

FIG. 2 is schematic illustration of another embodiment of the invention, wherein a plurality of flow cells 6,6, . . . respectively contained in electric ovens 5,5, . . . are connected to a valve oven 2 via a multi-way valve 200 so that samples removed from desired test pieces in separate flow cells 6 are carried in sequence to the valve oven 2 over a period of time and trapped in the trap tube 24 by following the same procedure as described above. This embodiment has a benefit in that samples from numerous test pieces can be efficiently sent in succession to an instrument for analysis, where they can be analyzed.

Figure 3:
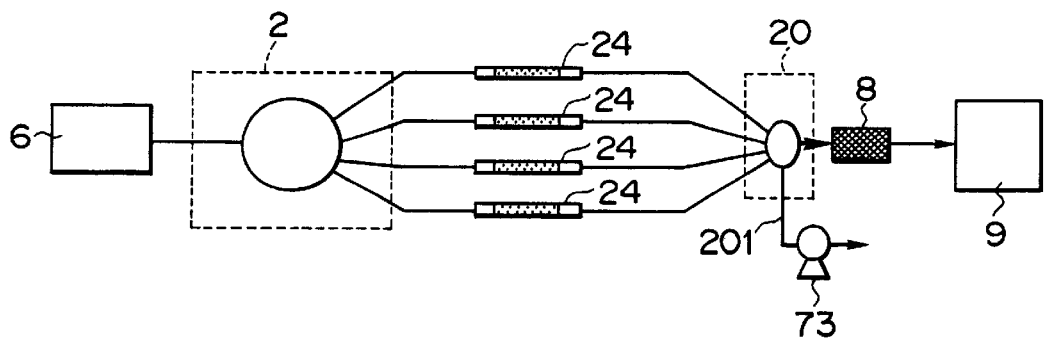
FIG. 3 is an enlarged schematic illustration of the principal part of yet another embodiment of the present invention.

FIG. 3 shows yet another embodiment of the invention, which has the same configuration as that of the embodiment shown in FIG. 1 except that a plurality of trap tubes 24,24, . . . are provided. To be more specific, a valve 20 is provided, and a desired number of trap tubes 24 are installed in the valve oven 2 or between the valve oven 2 and the valve 20 so that samples are respectively trapped in the separate trap tubes 24 and analyzed one after another over a period of time. The embodiment thus enables the accurate and reliable detection of numerous substances and measurement of the detected substances.

Figure 4:
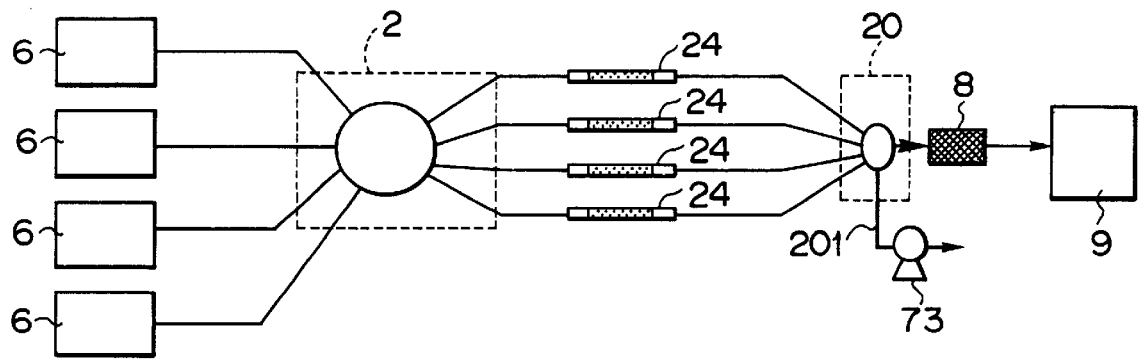
FIG. 4 an enlarged schematic illustration of the principal part of yet another embodiment of the present invention.

FIG. 4 shows yet another embodiment of the invention, wherein numerous flow cells 6,6, . . . are linked to the valve oven 2, and numerous trap tubes 24,24, . . . are installed in the valve oven 2 or between the valve oven 2 and the valve 20. As it is possible to simultaneously set numerous test pieces and collect samples that have been removed from the test pieces into a single or numerous trap tubes 24,24, . . . , this embodiment is very convenient for conducting an intensive analysis on a single sample or analyzing numerous samples automatically and/or successively over a period of time. Each embodiment shown in FIG. 2, 3, or 4 is capable of successive analysis and/or automatic analysis.

The upper graph (the normal line) in FIG. 5 represents a chromatogram resulting from analyzing a silicone wafer by using the embodiment shown in FIG. 1.

The test was performed under the following conditions:

| Test Conditions | |
| --- | --- |
| Gas Chromatograph | |
| column.: | TC-1; 60 m × 0.25 mm; df = 0.25 μm |
| column temperature: | 40–280° C. |
| carrier gas: | Hel. 6 kgf/cm$^2$ |
| MS Detector | |
| ionization voltage: | 70 eV |
| scan: | 20–450 |
| TCT | |
| cryofocusing temperature: | −130° C. |
| SWA | |
| trapping agent: | Tenax TA |
| trap line temperature: | 270° C. |
| cell purge gas flow rate: | 105 ml/min |
| backside exhaust flow rate: | 40 ml/min |
| trap flow rate: | 40 ml/min |

The chromatogram shows peaks of detection of DOP (dioctyl phthalate), which is a kind of plasticizers for plastics.

The lower graph (the deteriorated line) in FIG. 5 represents a chromatogram resulting from analysis performed on a silicone wafer by using a system similar to the embodiment shown in FIG. 1 and under the same conditions as those for the upper graph in FIG. 5, except that no inert gas flows from the direction opposite the direction from which the gas flows in the sample trapping line. The chromatogram shows the peak of detection of decomposed substances, which appears approximately 15 minutes after the initiation of the test and indicates thermal decomposition of DOP along the line, while showing almost no peaks of detection of DOP.

Therefore, it is evident that the inert gas which flows in the direction opposite the direction in which the gas flows in the sample trapping line produces a conspicuous difference in analysis results.

As explained above, the invention claimed in claim 1 or claim 2 calls for causing, except during the process of trapping organic compound samples attached to or contained in such a test piece as a silicone wafer or the like, a part of the inert gas flowing into a measuring unit, such as a flow cell, flows from the direction opposite the direction from which the inert gas flows during the sample trapping process. Therefore, there is no possibility of air, a blank gas, interfering particles, or the like entering the measuring unit. Furthermore, as measuring operation does not produce any change in temperature, this invention is capable of preventing deterioration of communicating passages, which may otherwise occur due to change in temperature when the system is used at high temperature. Thus, the invention is effective for protecting the system line, including the flow cell and the valve tubes, and makes it possible to maintain at such a temperature as to prevent condensation of organic compounds removed from test pieces, in other words within the range of about 200 to 350° C. As a result, the invention enables the high-performance analysis in the field of measuring organic compounds on a silicone wafer, a hard disk, other electronic components or the like.

The invention claimed in claim 3 or claim 4 calls for connecting the cell purge gas channel described above to a plurality of flow cells, thereby enabling the automatic analysis of a plurality of test pieces. Furthermore, by providing a plurality of trap tubes in order to permit samples to be successively collected in accordance with different temperatures at which the respective samples will be heated, the invention has outstanding benefits in that it is capable of successive analysis of samples as well as automatic analysis.

What is claimed is:

1. A method of trace analysis of organic compounds comprising the steps of:

removing organic compounds from a test piece by heating the test piece in a flow cell;

concentrating said organic compounds in a trap tube and removing the compounds from the trap tube by heating the trap tube; and introducing said organic compounds into a gas analyzer to be analyzed therein; wherein a purified inert gas is caused, except during the process of trapping the organic compounds, to flow into the flow cell from the direction opposite the direction from which the gas flows along the trapping line, said purified inert gas flowing into the cell via at least a communicating tube.

2. An apparatus for trace analysis of organic compounds comprising:

a flow cell so formed as to permit a test piece to be removably set therein and also permit a carrier as to flow therethrough;

a trap tube connected to said flow cell, which is brought into communication with said trap tube;

a detector connected to said trap tube; and a flow rate controller connected to said flow cell;

wherein a channel for a purified inert gas is provided between said flow rate controller and said flow cell and also between the flow rate controller and a sleeve that communicates with said flow cell.

3. An apparatus for trace analysis of organic compounds as claimed in claim 2, wherein said channel for an inert gas is connected to a plurality of flow cells.

4. An apparatus for trace analysis of organic compounds as claimed in claim 2, wherein said channel for the inert gas is connected to a plurality of trap tubes.

* * * * *